(12) United States Patent
Kim

(10) Patent No.: US 7,874,840 B2
(45) Date of Patent: Jan. 25, 2011

(54) FLEXIBLE DENTAL DAM AND METHODS OF USING SAME

(76) Inventor: Young K. Kim, 7760 Belden St., Apt. B-2, San Diego, CA (US) 92111

(*) Notice: Subject to any disclaimer, the term of this patent is extended or adjusted under 35 U.S.C. 154(b) by 145 days.

(21) Appl. No.: 11/894,820

(22) Filed: Aug. 22, 2007

(65) Prior Publication Data

US 2009/0053668 A1   Feb. 26, 2009

(51) Int. Cl.
*A61C 5/00* (2006.01)
(52) U.S. Cl. .................................. 433/215; 433/136
(58) Field of Classification Search .............. 433/29, 433/91, 93, 136, 137, 138, 215
See application file for complete search history.

(56) References Cited

U.S. PATENT DOCUMENTS

| | | | | |
|---|---|---|---|---|
| 6,024,566 A | * | 2/2000 | Bruns et al. ................. | 433/136 |
| 6,135,770 A | * | 10/2000 | Bembenek et al. ........... | 433/88 |
| 6,293,929 B1 | * | 9/2001 | Smith et al. ................. | 604/289 |
| 6,305,536 B1 | * | 10/2001 | Tanaka .................... | 206/316.2 |
| 2007/0148619 A1 | * | 6/2007 | Anderson ................... | 433/136 |

* cited by examiner

*Primary Examiner*—Cris L Rodriguez
*Assistant Examiner*—Eric Rosen

(57) ABSTRACT

A flexible dental dam for application in a variety of dental procedures, the flexible dental dam including a flexible dome having at least two apertures for inserting dental tools, and a flexible sheet bound between two rigid rings, wherein the flexible dome is attached to the flexible sheet at one of the two rigid rings. The flexible sheet can include an aperture for positioning around a tooth. Methods for use of the flexible dental dam are describe.

4 Claims, 4 Drawing Sheets

US 7,874,840 B2

FLEXIBLE DENTAL DAM AND METHODS OF USING SAME

CROSS-REFERENCE TO RELATED APPLICATIONS

None

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention relates to devices used in dentistry. More particularly, to dental dams used for oral procedures to protect from objects such as tooth fragments being swallowed or aspirated by the patient.

(2) Description of Related Art

A number of dental dams are available commercially and have been used over the years for procedures such as removing tooth decay and filling the cavities, preparing a tooth for a crown and the like. These dams usually comprise a plastic or metal frame on which is stretched a flexible sheet such as latex. The sheet is provided with a small diameter aperture about its center that can be stretched tightly about the tooth being drilled. The dam is usually sufficiently large to cover the mouth thereby preventing particulates produced during the dental operation from entering the mouth, throat or airway of the patient. Unfortunately, these dams are flat sheets of flexible material and are not designed to contain random trajectory high speed particles produced during grinding of a tooth nor do they protect the dentist or patient from being impacted by these particles nor is it designed to capture or entrap these particles for easy disposal and protection against transmittable diseases.

Consequently, there is a need for a dental dam that protects the patient from swallowing or aspirating fragments of teeth produced during the dental operation, the dentist and dental assistants from high speed particles ejected during drilling and other patients or dental personnel from diseases that could be transmitted by fragments of teeth that are not contained and properly discarded from infected patients.

BRIEF SUMMARY OF THE INVENTION

The present invention is a system for performing a dental procedure that reduces or eliminates particulates produced during the procedure from being deposited in the mouth of the patient or about the area where the dental procedure is performed comprising: an enclosed dental dam having a semi-rigid upper ring having a top side and a snap connector along its interior perimeter edge the top side having a first radially outward extending lip; a semi-rigid lower ring having a snap connector able to be received by the interior perimeter edge of the semi-rigid upper ring for holding a flexible sheet having an opening for sealing about a tooth and a bottom side having a second radially outward extending lip such that when the upper ring and the lower ring are connected the first radially outward extending lip and the second radially outward extending lip form a snap fit adapter; and a semi-flexible dome having an upper surface with at least two apertures and a base having a snap fit adapter along its inner perimeter edge able to be received by the snap fit adapter formed by the connected upper ring and lower ring; an air abrasive drill able to be received by one of the at least two apertures for removing tooth material; and a dental camera able to be received by the second of the two apertures for visualizing the tooth during the dental procedure.

In another aspect of the present invention an enclosed dental dam for use with an air abrasive drill comprising: a semi-rigid upper ring having a top side and a snap connector along its interior perimeter edge the top side having a first radially outward extending lip; a semi-rigid lower ring having a snap connector able to be received by the interior perimeter edge of the semi-rigid upper ring for holding a flexible sheet having an opening for sealing about a tooth and a bottom side having a second radially outward extending lip such that when the upper ring and the lower ring are connected the first radially outward extending lip and the second radially outward extending lip form a snap fit adapter; and a semi-flexible dome having an upper surface with at least two apertures and a base having a snap fit adapter along its inner perimeter edge able to be received by the snap fit adapter formed by the connected upper ring and lower ring the apertures having sufficient diameter to receive a dental camera and an air abrasive drill.

In yet another aspect of the present invention is a method for performing a dental procedure using an enclosed dental dam described above comprising, securing a flexible sheet with an aperture between the semi-rigid upper ring and the semi-rigid lower ring creating a dam; fitting the dam about a tooth; affixing the dome to the outer perimeter edge of the dam; and inserting the dental camera and air abrasive drill through the two apertures in the dome.

In one embodiment of each of these aspects of the invention the dome may comprise three apertures, one for receiving an air abrasive drill, one for a dental camera and one for a suction tube to remove tooth material and abrasive resulting from the dental procedure.

In another embodiment of these aspects of the present invention a dental procedure includes but is not limited to filling a cavity or affixing a cap to a tooth.

DETAILED DESCRIPTION OF THE INVENTION

Figure 1:
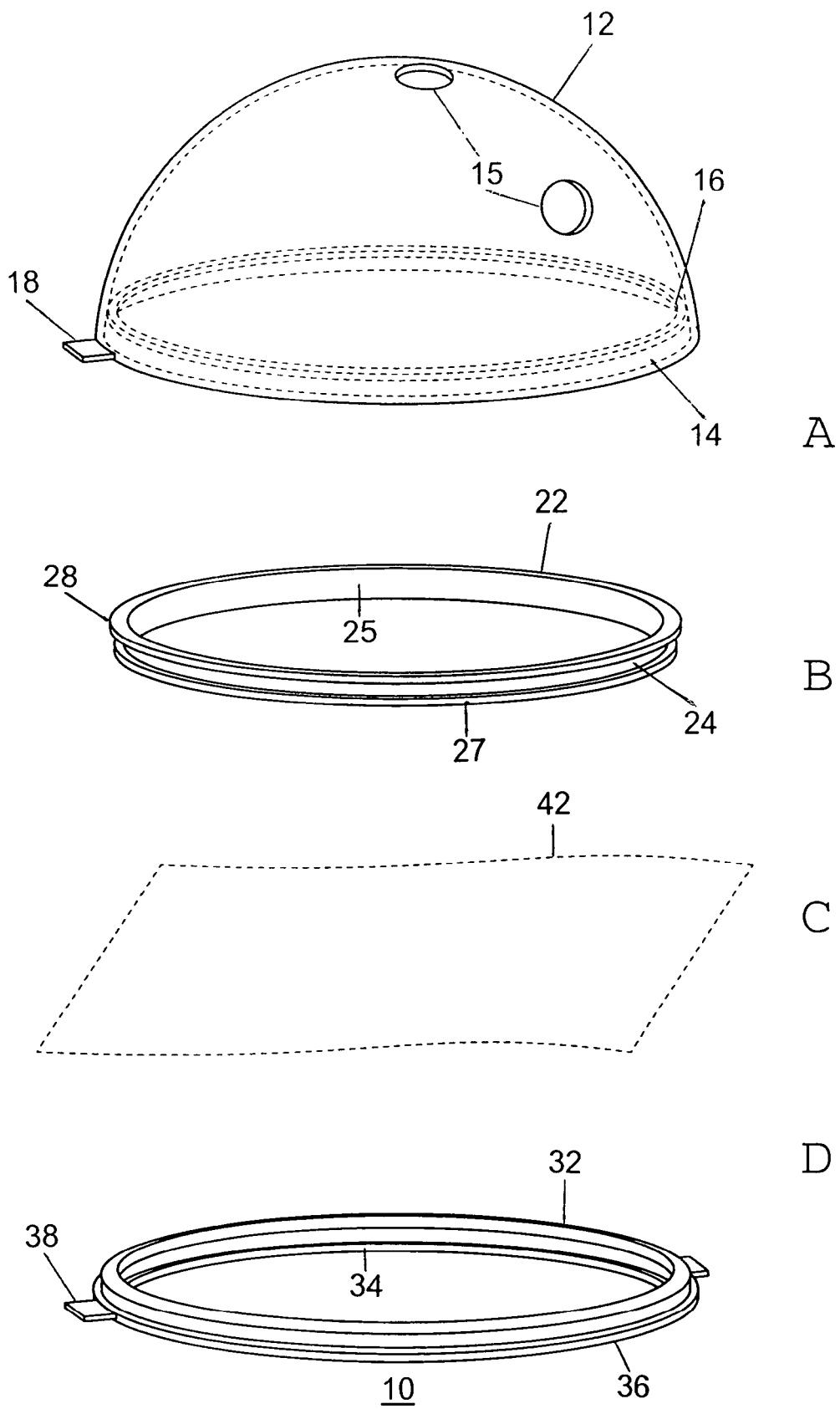
FIG. 1 is an exploded perspective view of the (A) dome, (B) semi-rigid upper ring and (C) flexible sheet and (D) semi-rigid lower ring of the enclosed dental dam of the present invention.
Figure 2:
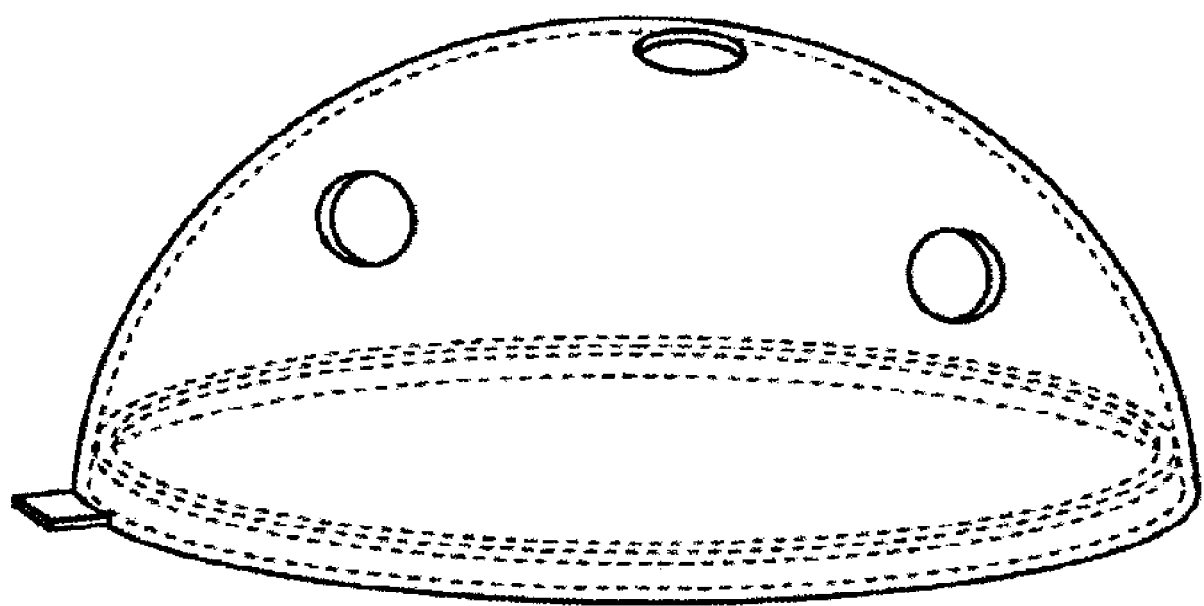
FIG. 2 is a perspective view of a dome having three apertures
Figure 3:
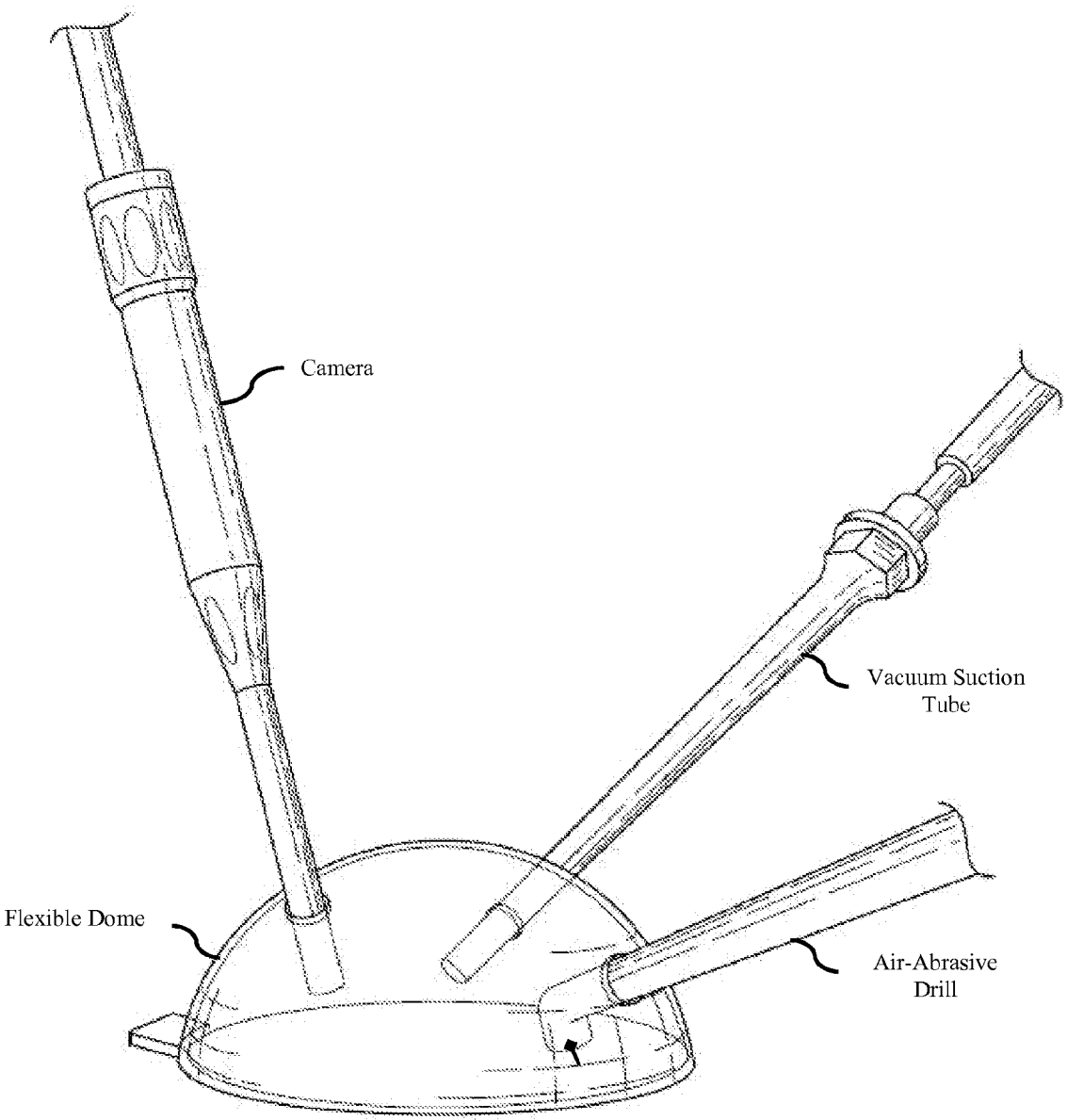
FIG. 3 illustrates a side view of a flexible dome comprising three apertures, each aperture is individually adapted to receive a dental tool selected from a camera, vacuum suction tube, and air-abrasive drill.
Figure 4:
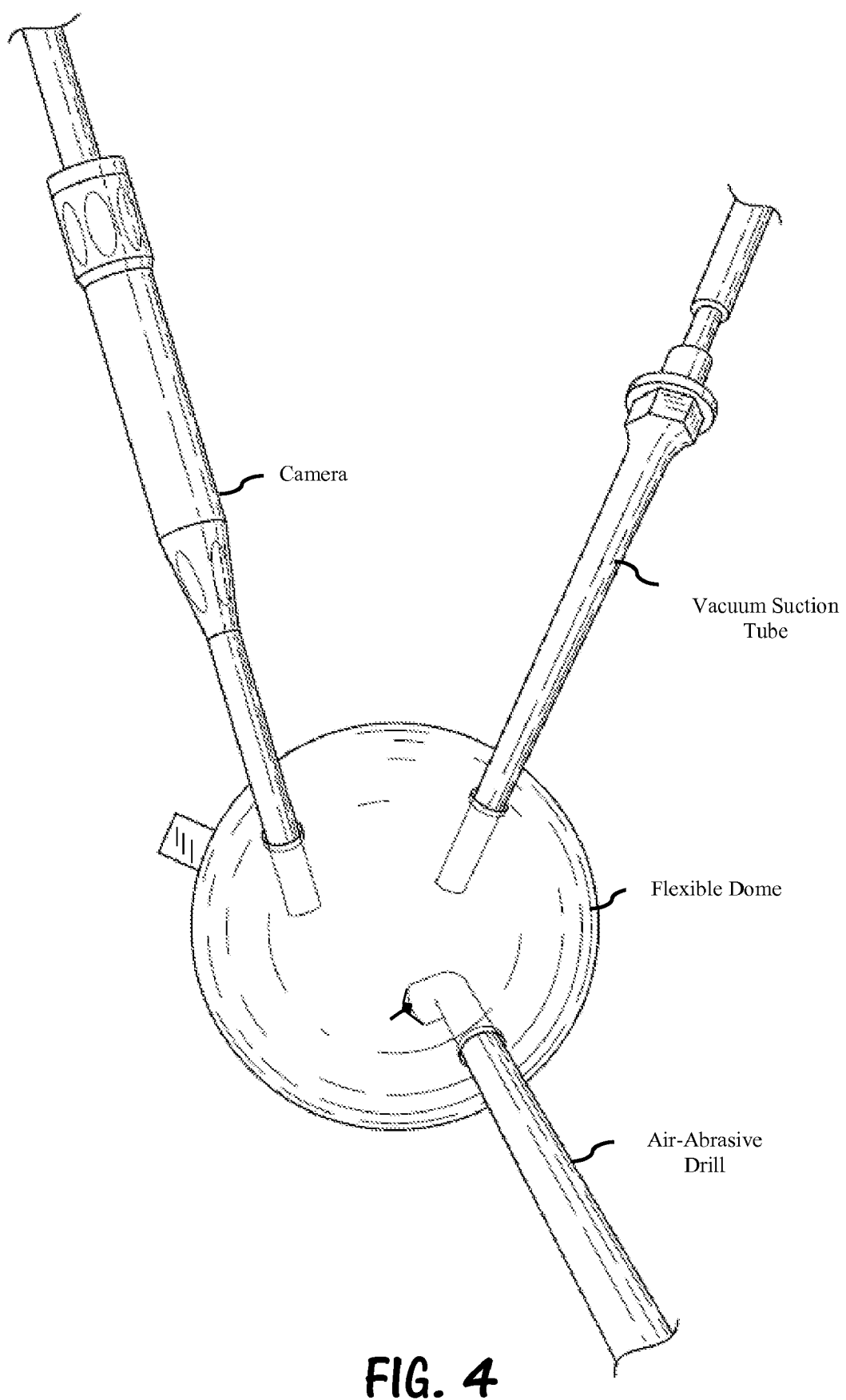
FIG. 4 illustrates a tip view of flexible dome comprising three apertures, each aperture is individually adapted to receive a dental tool selected from a camera, vacuum suction tube, and air-abrasive drill.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "snap connector" as used herein refers to any connection that can secure a thin sheet of flexible material such as latex between the two elements that are to be joined by the connectors such as the semi-rigid upper and lower rings of the present invention. One preferred snap connector is prepared by providing a groove on one of the joining elements and a ridge that fits snugly into the groove on the other joining element when a flexible sheet is secured between them.

The term "dome" as used herein refers to a shape similar to a half of a sphere or a hemisphere. In the present invention the base of the dome can be round but is not limited to this configuration. The base of the dome could be for example elliptical, oval, square, and rectangular or any combination thereof.

The term "aperture" as used herein refers to an opening through an element of the invention such as the apertures provided in the semi-flexible dome. The apertures are preferably round but may be provided in any number of desirable shapes that allow access by other dental tools such as the dental camera or the air abrasive drill. It is also preferable that the shape conform to the shape of the device being inserted through the aperture to assure a tight seal preventing tooth or abrasive material from escaping the enclosed dental dam.

The term "dental procedure" as used herein refers to any dental work that is usually performed with the non-enclosed dams available commercially including removal of decayed tooth enamel or dentin and filling the cavity and preparing a tooth for a cap.

The present invention is a system for performing a dental procedure that reduces or eliminates particulates produced during the procedure from being deposited in the mouth of the patient or about the area where the dental procedure is performed comprising: a semi-rigid upper ring, a semi-rigid lower ring and a dome. The semi-rigid upper ring having a snap connector along its interior perimeter edge and a top side having a first radially outward extending lip. The semi-rigid lower ring having a snap connector able to be received by the interior perimeter edge of the semi-rigid upper ring for holding a flexible sheet having an opening for sealing about a tooth and a bottom side having a second radially outward extending lip. When the upper ring and the lower ring are connected the first radially outward extending lip and the second radially outward extending lip form a snap fit adapter. The semi-flexible dome having an upper surface with at least two apertures and a base having a snap fit adapter along its inner perimeter edge able to be received by the snap fit adapter formed by the connected upper ring and lower ring. An air abrasive drill is able to be received by one of the at least two apertures for removing tooth material; and a dental camera able to be received by the second of the two apertures for visualizing the tooth during the dental procedure.

Upper Ring

The semi-rigid upper ring 22 is made of a material that allows bending and flexing during use, preferably plastic or polymer. This flexibility permits ease of connecting the lower ring 22 when securing the flexible sheet 42 between the rings 22 and 32. In addition, because the size and shape of the oral cavity will vary significantly from patient to patient this flexibility allows the device 10 to be easily fitted about the mouth of most, if not all patients.

The ring 22 may be provided in a number of shapes and sizes which will depend on the size and shape of the oral cavity and the type of dental procedure to be performed. Desirable shapes may include for example, triangular, square, rectangular, oval, elliptical or round. Preferably the semi-rigid upper ring 22 is round and be provided in diameters ranging from about 1.5 to about 6.0 inches. Increased diameter sizes may be provided for procedures requiring a larger dam and for larger oral cavities.

The semi-rigid upper ring 22 may be provided in a variety of configurations that allow it to be connected to the semi-rigid lower ring 32 securing a flexible sheet 42 between the rings and for providing a portion of the snap fit adapter for receiving the dome 12 along it's exterior perimeter edge 24. In a preferred embodiment the interior perimeter edge 25 has one portion of a snap connector such as a snap connector ridge 27. This ridge 27 receives a complimentary groove snap connector 34 present on the interior of the semi-rigid lower ring 32. Correspondingly, the top of the upper ring 22 provides a first radially outward extending lip 28 as one portion of the snap fit adapter that receives the interior base ridge 14 of the dome 12.

Lower Ring

As with the semi-rigid upper ring 22 the semi-rigid lower ring 32 is made of a material that allows bending and flexing during use, preferably plastic or polymer. This flexibility permits ease of connecting the semi-rigid upper ring 22 when securing the flexible sheet 42 between the rings 22 and 32. In addition, because the size and shape of the oral cavity will vary significantly from patient to patient this flexibility allows the device 10 to be easily fitted about the mouth of most, if not all patients. Preferably the semi-rigid lower ring 32 is made of the same material as the semi-rigid upper ring 22 and of a slightly smaller diameter to allow the flexible sheet 42 to be secured between the two rings when snap connected together.

The semi-rigid lower ring 32 may be provided in a number of shapes and sizes which will depend on the size and shape of the oral cavity, the type of dental procedure to be performed and the size and shape of the semi-rigid upper ring 22. In a preferred configuration the semi-rigid lower ring 32 and upper ring 22 are round.

The semi-rigid lower ring 32 may be provided in a variety of configurations that allow it to be connected to the semi-rigid upper ring 22 securing a flexible sheet 42 between the rings and providing the remaining portion of the snap fit adapter for receiving the dome 12 along it's exterior perimeter edge. In a preferred embodiment the interior perimeter edge has the complimentary portion of a snap connector on the semi-rigid upper ring 22 such as a snap connector groove 34. This groove 34 is received by the complimentary ridge snap connector 27 present on the interior of the semi-rigid upper ring 22. In addition, the bottom side of the semi-rigid lower ring 32 provides the second radially outward extending lip 36. These lips 28 and 36 form the groove that receives the ridge 16 on the base of the flexible dome 14 when the semi-rigid upper 22 and lower rings 32 are connected. When sufficient pressure is applied the ridge 16 at the base of the flexible dome 14 it snaps into the groove formed when the semi-rigid upper 22 and lower rings 32 are connected forming an enclosed dental dam.

The semi-rigid lower ring 32 may further comprise a tab 38 integral to and along the second radially outward extending lip 36 to assist in separating the semi-rigid upper 22 and lower rings 32 when connected. The tap 38 radiates outward from the center of the ring and is preferably a length and width that allows for ease of grasping. It may be provided in a variety of configurations from square, rectangular to semi-circular. In a preferred embodiment the tap 38 is not less than about ⅛ inch in width and not more than about ¾ inch. Preferable it is about ¼ inch. The tap 38 may have a length not less than about 3/16 inch and not more than 1 inch. Preferably the length is about ½ inch.

Dome

The semi-flexible dome 12 is made of a material that is at least as pliable as the semi-rigid upper 22 and lower rings 32. Preferably the dome 12 is more flexible then the semi-rigid upper 22 and lower rings 32 to permit tight sealing about the camera and air abrasive drill when inserted through the apertures 15. This flexibility also allows the dome 12 to be more easily secured via snap fit adapter to the connected semi-rigid upper 22 and lower rings 32. In addition, the size and shape of the oral cavity will vary significantly from patient to patient, consequently, this flexibility allows the device 10 to be easily fitted about the mouth of most, if not all patients.

The dome 12 may be provided in a number of shapes and sizes which will depend on the size and shape of the oral cavity, the type of dental procedure to be performed and the size and shape of the semi-rigid upper 22 and lower rings 32. Preferably the dome 12 has a circular base when the semi-rigid upper 22 and lower rings 32 are round. The diameter of the dome base 14 may be smaller than the diameter of the connected semi-rigid upper 22 and lower rings 32 to provide a secure fit.

The dome 12 may be provided in a variety of configurations that allow it to be affixed through the snap fit adapter formed when the semi-rigid upper 22 and lower rings 32 are connected. In a preferred embodiment the interior perimeter edge of the base 14 has the complimentary portion of a snap fit adapter such as a snap fit ridge 16. This ridge 16 is received by the complimentary snap fit groove formed by the first 28 and second radially outward extending lips 36 of the connected semi-rigid upper 22 and lower rings 32. When sufficient pressure is applied the ridge 16 at the base of the flexible dome 14 it snaps into the groove formed by the connected semi-rigid rings 22 and 32 creating an enclosed dental dam.

The dome 12 may further comprise a tab 18 integral to and along the base 14 to assist in separating it from the semi-rigid upper 22 and lower rings 32. The tap 18 radiates outward from the exterior perimeter edge of the base and is preferably a length and width that allows for ease of grasping. It may be provided in a variety of configurations including for example square, rectangular or semi-circular. In a preferred embodiment the tap 18 is not less than about ⅛ inch in width and not more than about ¾ inch. Preferable it is about ¼ inch. The tap 18 may have a length not less than about 3/16 inch and not more than 1 inch. Preferably the length is about ½ inch.

Use

The lower and upper rings may be assembled with a flexible sheet secured between them for immediate use or the rings and flexible sheet may be provided separately. If separate, the flexible sheet, preferably latex is laid over the lower ring. The upper ring is then press fit onto the lower ring securing the latex sheet between them. The aperture of the latex sheet is then stretched about the tooth and the dam base secured in place. The dome is then positioned over the dam base and snap fit within or about the patient's mouth. The dental camera and air abrasive drill are then inserted into the apertures provided in the dome. Once the image from the camera appears on the view screen the procedure may begin. If a suction tube is desired an additional aperture may be provided in the dome and the tube inserted when the camera and air abrasive drill are inserted.

Particulates containing tooth material and abrasive are captured within this enclosure and removed when the dam is released from about the tooth. Alternatively tooth material and abrasive can be removed by air suction if a suction tube is utilized. While the enclosed dental dam of the present invention can be reused after sterilization it is preferable that the device be disposable.

I claim:

1. A dental dam adapted for enclosing an area about a tooth during a dental procedure, comprising:
    a snap connector, comprising:
        a flexible upper ring having:
            a first interior perimeter edge, and a first exterior perimeter edge disposed opposite of said first interior perimeter edge,
            said upper ring further having a top portion and a bottom portion, and comprising:
                a snap connector ridge extending radially outwardly from said bottom portion of said first exterior perimeter edge along a first circumference thereof, and
                a first lip extending radially outwardly from said top portion of said first exterior perimeter edge along said first circumference;
        a flexible lower ring having:
            a second interior perimeter edge, and a second exterior perimeter edge disposed opposite of said second interior perimeter edge,
            said lower ring further having a top portion and a bottom portion, and comprising
                a snap connector groove extending radially inward from said second interior perimeter edge along a second circumference thereof, said snap connector groove adapted for receiving said snap connector ridge of said flexible upper ring; and
                a second lip extending radially outwardly from said bottom portion of said second exterior perimeter edge along said second circumference; and
        a flexible sheet adapted to be disposed therebetween;
        said first and second lips adapted for positioning about opposite sides of said second exterior perimeter edge to define a snap fit groove; and
    a flexible dome having an upper surface, and a base;
        said base further comprising a snap fit ridge extending radially inward from an interior perimeter edge of said base, and at least one tab extending radially outwardly from an exterior perimeter edge of said base;
        said upper surface further comprising:
            a first aperture adapted to receive a camera;
            a second aperture adapted to receive a suction tube; and
            a third aperture adapted to receive an air-abrasive drill;
            said first aperture, second aperture, and third aperture are each further adapted to form a tight seal about one of said camera, suction tube, and air-abrasive drill;
    wherein said snap fit groove of said snap connector is adapted to receive said snap fit ridge of said flexible dome to form a dental dam adapted for enclosing an area about a tooth.

2. A method of performing a dental procedure, comprising the steps of:
    providing components of a dental dam adapted for enclosing an area about a tooth, the components including a semi-rigid upper ring, a semi-rigid lower ring and a flexible sheet for disposing therebetween, and a flexible dome having an upper surface with at least two apertures each adapted for receiving a dental tool; wherein the flexible sheet has an opening for sealing about a tooth, and wherein the upper surface of the dome is flexible and permits a tight seal between each of said apertures and a dental tool selected from the group consisting of: an air abrasive drill, a dental camera, and a suction tube, securing the flexible sheet between the semi-rigid upper ring and the semi-rigid lower ring, fitting the flexible sheet about a tooth, affixing the flexible dome to an outer perimeter edge of the upper ring to construct a dental dam adapted for enclosing an area about a tooth, inserting a first dental tool into the dental dam at a first of said at least two apertures, said first aperture forming a tight seal with said first dental tool, inserting a second dental tool into the dental dam at a second of said at least two apertures, said second aperture forming a tight seal with said second dental tool, performing a dental procedure within said dental dam, and capturing particulate within the enclosed dental dam.

3. The method of claim 2, wherein the dental procedure is one of:

filling a cavity or affixing a cap to a tooth.

4. The method of claim 3, said dental procedure including the step of:

substantially eliminating ejection of said particulate into a patients mouth or about an area where said dental procedure is performed.

* * * * *